United States Patent [19]

Krämer et al.

[11] 4,427,673
[45] Jan. 24, 1984

[54] AZOLYLALKYL KETONE AND ALCOHOL FUNGICIDES

[75] Inventors: Wolfgang Krämer, Wuppertal; Karl H. Büchel, Burscheid; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 291,003

[22] Filed: Aug. 7, 1981

[30] Foreign Application Priority Data

Aug. 27, 1980 [DE] Fed. Rep. of Germany ....... 3032326

[51] Int. Cl.³ .................... A01N 43/50; A01N 43/64; C07D 233/61; C07D 249/08
[52] U.S. Cl. .................... 424/245; 424/232; 424/269; 424/273 R; 548/101; 548/262; 548/341
[58] Field of Search .................. 548/101, 262, 341; 424/245, 269, 273 R

[56] References Cited

U.S. PATENT DOCUMENTS

| | | | |
|---|---|---|---|
| 3,872,117 | 3/1975 | Meiser et al. | 548/341 |
| 4,297,364 | 10/1981 | Sauter et al. | 424/269 |
| 4,331,674 | 5/1982 | Kramer et al. | 424/269 |
| 4,349,556 | 9/1982 | Timmler et al. | 424/269 |

FOREIGN PATENT DOCUMENTS

| | | | |
|---|---|---|---|
| 7505 | 2/1980 | European Pat. Off. | |
| 7506 | 2/1980 | European Pat. Off. | |
| 2635663 | 2/1978 | Fed. Rep. of Germany | 548/262 |
| 2734426 | 2/1978 | Fed. Rep. of Germany | 424/269 |
| 7603195 | 9/1976 | France | |
| 2323689 | 4/1977 | France | 548/262 |

*Primary Examiner*—Alton D. Rollins
*Attorney, Agent, or Firm*—Sprung, Horn, Kramer & Woods

[57] ABSTRACT

Fungicidally active novel azolylalkyl derivatives of the formula

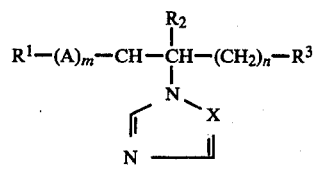

in which
  $R^1$ is an alkyl or aryl group,
  $R^2$ is a hydrogen atom or an alkyl or aryl group,
  $R^3$ is cyano or —CO—OR$^4$,
  $R^4$ is alkyl or aralkyl group,
  A is a keto group or a CH(OH) group,
  X is a nitrogen atom or the CH group, and
  m and n are identical and represent 0 to 1, or a physiologically acceptable addition product thereof with an acid or a metal salt.

15 Claims, No Drawings

AZOLYLALKYL KETONE AND ALCOHOL FUNGICIDES

The present invention relates to certain new azolylalkyl derivatives, to several processes for their production and to their use as fungicides.

It has already been disclosed that various azo derivatives, such as 1-(4-chlorophenyl)-4,4-dimethyl-2-(1,2,4-triazol-1-yl)-pentan-3-one, 2-acetoxy-3,3-dimethyl-1-(3-trifluoromethylphenoxy)-1-(1,2,4-triazol-1-yl)-butane, 1-triphenylmethyl-imidazole and 1-(4-chlorophenoxy)-2-(4-chlorobenzyloxy)-3,3-(dimethyl-1-imidazol-1-yl-butane have good fungicidal properties (see DE-OS (German Published Specification) 2,734,426, U.S. Pat. Nos. 4,145,428, 3,321,366, and 4,229,459. However, the action of these compounds is not always completely satisfactory, especially when low amounts and concentrations are applied.

The present invention now provides, as new compounds, the azolylalkyl derivatives of the general formula

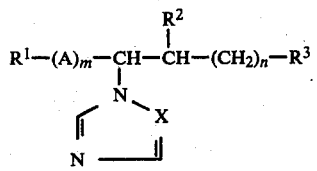

in which
R$^1$ represents an alkyl or aryl group,
R$^2$ represents a hydrogen atom or an alkyl or aryl group,
R$^3$ represents a cyano group or a —CO—OR$^4$ grouping,
wherein
R$^4$ represents an alkyl or aralkyl group, and
A represents a keto group or a CH(OH) grouping,
X represents a nitrogen atom or a CH group and
m and n are identical and represent 0 or 1, and physiologically acceptable acid addition salts and metal salt complexes thereof.

In some cases, the compounds of the formula (I) have asymmetric carbon atoms; they can then exist in the form of various geometric isomers, which can be obtained in various proportions. In both cases, they exist in the form of optical isomers. The invention relates to all the isomers.

According to the present invention there is further provided a process for the production of a compound of the present invention characterized in that
(a) anazolyl-ketone of the formula

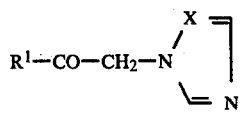

in which R$^1$ and X have the abovementioned meanings, is reacted with an alkene of the general formula $$R^2-CH=CH-R^3 \quad (III)$$

in which R$^2$ and R$^3$ have the abovementioned meanings, in the presence of a diluent and in the presence of a base, and if appropriate in the presence of a catalyst, and, if a compound of the present invention in which A denotes CH(OH) is required, the azolylalkyl-keto derivative formed, of the general formula

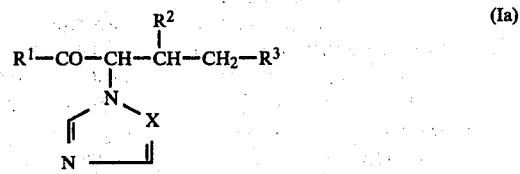

in which R$^1$, R$^2$, R$^3$ and X have the abovementioned meanings, is then reduced, or
(b) an alkene of the general formula

in which R$^1$, R$^2$ and R$^3$ have the abovementioned meanings, is reacted with an azole of the general formula

in which X has the abovementioned meaning, in the presence of a diluent and in the presence of a base, and if appropriate in the presence of a catalyst; and the compound of formula (I) obtained by process variant (a) or (b) is converted, if desired, into an acid addition salt thereof or a metal salt complex thereof.

In some cases, it proves to be advantageous to obtain the compounds of the formula (I) in a pure form via their salts.

The preferred azolylalkyl derivatives of the present invention of the general formula

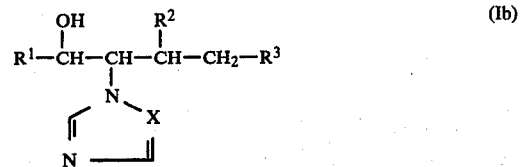

in which R$^1$, R$^2$, R$^3$ and X have the abovementioned meaning, are interesting intermediate products. Derivatives on the OH group can be formed in the customary manner, such as by etherification, acylation or carbamoylation.

The new azolylalkyl derivatives of the present invention have powerful fungicidal properties. Surprisingly, the compounds according to the invention have a considerably more powerful action than known azole derivatives, for example those mentioned initially, which are closely related compounds from the point of view of their action. The substances according to the invention thus represent an enrichment of the art.

Preferred azolylalkyl derivatives according to the present invention are those in which
R$^1$ represents straight-chain or branched alkyl group with 1 to 4 carbon atoms or an optionally substituted aryl group with 6 to 10 carbon atoms (such as, preferably, phenyl, preferred substituents which may be mentioned being: halogen, alkyl with 1 to 4 crbon atoms, halogenoalkyl with 1 or 2 carbon atoms and 1 to 5 identical or different halogen atoms, such as, preferably, fluorine and chlorine atoms, alkoxy and alkylthio with in each case 1 or 2 carbon atoms, and phenyl), $R^2$ represents a hydrogen atom or a straight-chain or branched alkyl group with 1 to 4 carbon atoms or an optionally substituted aryl group with 6 to 10 carbon atoms (such as, preferably, phenyl, preferred possible substituents being the substituents on phenyl which have already been mentioned in the case of $R^1$), $R^3$ represents a cyano group or a —CO—OR$^4$ grouping, in which $R^4$ represents a straight-chain or branched alkyl group with 1 to 4 carbon atoms or an optionally substituted aralkyl group with 6 to 10 carbon atoms in the aryl part and 1 or 2 carbon atoms in the alkyl part (such as, preferably, benzyl, preferred possible substituents being the substituents on phenyl which have already been mentioned in the case of $R^1$), and A, X m and n have the abovementioned meanings.

Particularly preferred compounds of the formula (I) are those in which $R^1$ represents a tert.-butyl or isopropyl group, or a phenyl group which is optionally substituted by fluorine, chlorine, methyl, isopropyl, methoxy, methylthio, trifluoromethyl or phenyl;

$R^2$ represents a hydrogen atom, a methyl, ethyl, n-propyl or isopropyl group, or a phenyl group which is optionally substituted by fluorine, chlorine, methyl, ethyl, isopropyl, methoxy or phenyl;

$R^3$ represents a cyano group or a —CO—OR$^4$ grouping; in which $R^4$ represents a methyl, ethyl or propyl group, or a benzyl group which is optionally substituted by fluorine, chlorine or methyl; and A, X, m and n have the abovementioned meanings.

The following compounds of the general formula (I) may be mentioned specifically, in addition to the compounds mentioned in the preparative examples hereinbelow:

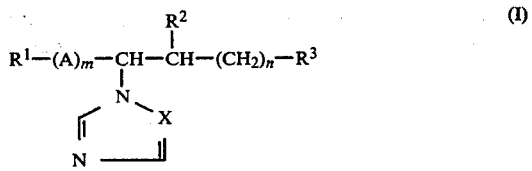

| $R^1$ | $(A)_m$ | $R^2$ | n | $R^3$ | X |
|---|---|---|---|---|---|
| $(H_3C)_3C$ | CO | $CH_3$ | 1 | —CO—$OC_2H_5$ | N |
| $(H_3C)_3C$ | CH(OH) | $CH_3$ | 1 | —CO—$OCH_3$ | N |
| $(H_3C)_3C$ | CO | $CH_3$ | 1 | —CO—$OC_2H_5$ | CH |
| $(H_3C)_3C$ | CH(OH) | $CH_3$ | 1 | —CO—$OCH_3$ | CH |
| 2,4-dichlorophenyl | CO | H | 1 | —CN | N |
| 2,4-dichlorophenyl | CH(OH) | H | 1 | —CN | N |
| 2,4-dichlorophenyl | CO | H | 1 | —CN | CH |
| 2,4-dichlorophenyl | CH(OH) | H | 1 | —CN | CH |
| 4-chlorophenyl | — | 4-chlorophenyl | 0 | —CN | N |
| phenyl | — | 4-chlorophenyl | 0 | —CO—$OCH_3$ | N |
| 2-chlorophenyl | — | 4-chlorophenyl | 0 | —CO—$OCH_3$ | N |
| 2,4-dichlorophenyl | — | 4-chlorophenyl | 0 | —CO—$OCH_3$ | N |
| $(H_3C)_3C$ | CH(OH) | $C_2H_5$ | 1 | —CO—$OC_2H_5$ | N |
| $(H_3C)_3C$ | CO | $C_3H_7$—n | 1 | —CO—$OC_2H_5$ | N |
| $(H_3C)_3C$ | CO | $C_3H_7$—iso | 1 | —CO—$OC_2H_5$ | N |

-continued

| R¹ | (A)ₘ | R² | n | R³ | X |
|---|---|---|---|---|---|
| (H₃C)₃C | CO | —C₆H₄—C₆H₅ | 1 | —CO—OCH₃ | N |
| (H₃C)₃C | CO | —C₆H₄—C₃H₇—iso | 1 | —CO—OCH₃ | N |
| 2-Cl-C₆H₄— | — | —C₆H₄—OCH₃ | 0 | —CO—OCH₃ | N |
| 4-Cl-C₆H₄— | — | —C₆H₅ | 0 | —CN | N |
| 4-Cl-C₆H₄— | — | 2,6-Cl₂-C₆H₃— | 0 | —CN | N |
| 4-Cl-C₆H₄— | — | —C₆H₄—Cl | | —CN | N |
| 4-Cl-C₆H₄— | — | CH₃ | 0 | —CO—OCH₃ | N |

If, for example, imidazol-1-yl-pinacolin and cinnamonitrile are used as starting substances the course of the reaction for the preparation of compounds of the invention is illustrated by the following equation (process variant (a)):

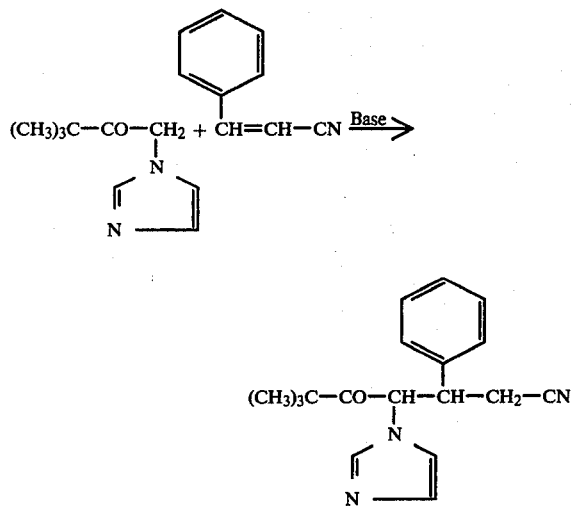

If, for example, 6-cyano-2,2-dimethyl-4-imidazol-1-yl-5-phenyl-3-hexanone and sodium borohydride are used as starting substances, the course of the reaction for the preparation of compounds of the invention is illustrated by the following equation (process variant (a)) (reduction step):

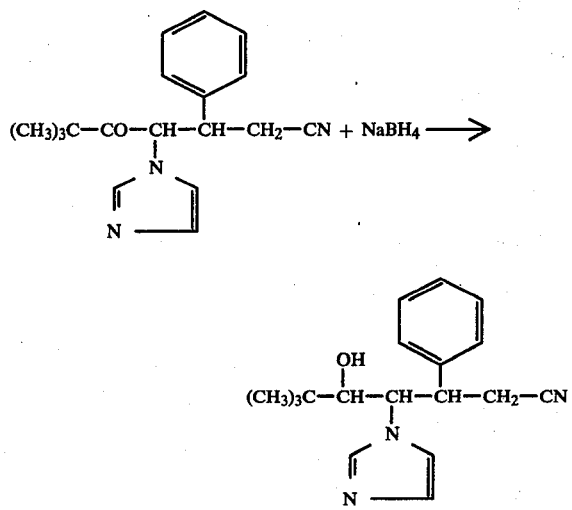

If, for example, 3-(4-methoxyphenyl)-2-phenylacrylic acid methyl ester and 1,2,4-triazole are used as starting substances, the course of the reaction for the preparation of compounds of the invention is illustrated by the following equation (process variant (b)):

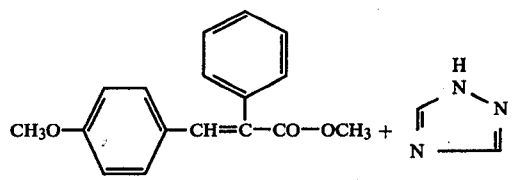

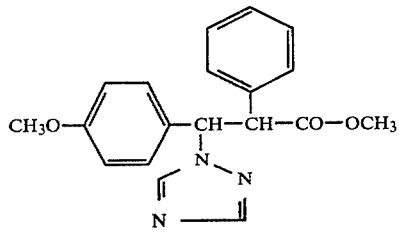

Particularly preferred azolyl-ketones to be used as starting compounds of formula (II) for process variant (a) according to the invention are those in which $R^1$ and X represent the radicals which have already been mentioned for these substituents in the description of the preferred and particularly preferred compounds of the present invention.

The azolyl-ketones of the formula (II) are known see U.S. application Ser. No. 792,756, filed May 2, 1977, DE-OS (German Published Specification) 2,610,022 and DE-OS (German Published Specification) 2,638,470). They can be prepared by customary methods, by reacting the corresponding halogenoketones with 1,2,4-triazole or imidazole in the presence of an acid-binding agent.

Particularly preferred alkenes also to be used as starting compounds of formula (III) for process variant (a) according to the invention are those in which $R^2$ and $R^3$ represent the radicals which have already been mentioned for these substituents in the description of the preferred and particularly preferred compounds of the present invention.

The alkenes of the formula (III) are generally known compounds of organic chemistry.

Particularly preferred alkenes to be used as starting compounds of formula (IV) for process variant (b) according to the invention are those in which $R^1$, $R^2$ and $R^3$ represent the radicals which have already been mentioned for those substituents in the description of the preferred and particularly preferred compounds of the present invention.

The alkenes of the formula (IV) are generally known compounds of organic chemistry. They are obtained, for example, by a Perkin synthesis and subsequent esterification (see Houben-Weyl, Methoden der organischen Chemie (Methods of Organic Chemistry), Volume 8, page 442 et seq).

The azoles of the formula (V) which are also to be used as starting substances for process variant (b) according to the invention are likewise generally known compounds of organic chemistry.

Organic solvents are possible diluents for the reactions, according to the invention, in process variants (a) and (b). These solvents include, preferably, alcohols (such as methanol, ethanol or isopropanol); aromatic hydrocarbons (such as benzene or toluene); ethers (such as tetrahydrofuran or dioxane); and nitriles (such as acetonitrile).

The reactions, according to the invention, in process variants (a) and (b) are carried out in the presence of a base. These bases include, preferably, akali metal alcoholates (such as sodium methylate, sodium ethylate or potassium methylate); alkali metal hydroxides (such as sodium hydroxide or potassium hydroxide); and alkali metal fluorides (such as sodium fluoride or potassium fluoride).

If appropriate, the reactions, according to the invention, in process variants (a) and (b) are carried out in the presence of a catalyst. These catalysts include, preferably, all the customary macrocyclic polyethers ("crown compounds").

The reaction temperatures can be varied within a substantial range in carrying out process variant (a) and (b). In general, the reactions are carried out at a temperature between 10° and 150° C., preferably at the boiling point of the solvent used.

Equimolar amounts of compounds of formulae (II) and (III) are preferably used in carrying out reaction variant (a) according to the invention. The compounds of the formula (I) are isolated in the customary manner.

In carrying out process variant (b) according to the invention, 1 to 4 moles of the azole of formula (V) are preferably employed per mole of alkene of the formula (IV). The compounds of the formula (I) are likewise isolated in the customary manner.

The optional reduction of process variant (a) is carried out in the customary manner, for example by reaction with complex hydrides, if appropriate in the presence of a diluent.

If complex hydrides are used, polar organic solvents are possible diluents for the reaction according to the invention. These solvents include, preferably, alcohols (such as methanol, ethanol, butanol or isopropanol) and ethers (such as diethyl ether or tetrahydrofuran). The reaction is in general carried out at 0° to 30° C., preferably at 0° to 20° C. For this reaction, about 1 mole of a complex hydride (such as sodium borohydride or lithium alanate) is employed per mole of the ketone of the formula (Ia). In order to isolate the reduced compounds of the formula (I), the residue is taken up in dilute hydrochloric acid and the mixture is then rendered alkaline and extracted with an organic solvent. Further working up is effected in the customary manner.

The following acids can preferably be used for the preparation of physiologically acceptable acid addition salts of the compounds of the formula (I): hydrogen halide acids (such as hydrobromic acid and, preferably, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid), and sulphonic acids (such as p-toluenesulphonic acid and 1,5-naphthalenedisulphonic acids). The acid addition salts of the compounds of the formula (I) can be obtained in a simple manner by customary salt formation method, for example by dissolving a compound of the formula (I) in a suitable inert solvent and adding the acid, for example hydrogen chloride, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Possible anions of the salts are those which preferably, are derived from the following acids: hydrogen halide acids (such as hydrochloric acid and hydrobromic acid), phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be purified in a known manner, for example by filtration, isolation and, if appropriate, by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as rust and powdery mildew; Venturia species, such as against the apple scab causative organism (*Fusicladium dendriticum*); and Podosphaera species, such as against the powdery mildew of apple causative organism (*Podosphaera leucotricha*).

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist-formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are generally required at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

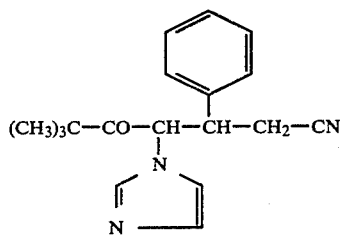

(1)

(Process variant (a))

6.6 g of sodium methylate in 66 ml of methanol were added to 25.8 g (0.2 mole) of cinnamonitrile and 33.2 g (0.2 mole) of imidazol-1-yl-pinacolin in 200 ml of methanol and the mixture was heated under reflux for 44 hours. The solvent was then distilled off in vacuo, the residue was taken up in water and the mixture was rendered neutral with 2 N hydrochloric acid. The aqueous phase was extracted twice with 100 ml of methylene chloride each time, the organic phase was then washed three times with 100 ml of water each time, dried over sodium sulphate and concentrated and the residue was dissolved in 500 ml of acetone. 36 g of 1,5-naphthalenedisulphonic acid, dissolved in 200 ml of acetone, were added and the precipitate formed was filtered off. This precipitate was taken up in 500 ml of methylene chloride and the mixture was stirred with 1 liter of saturated sodium bicarbonate solution. The organic phase was separated off, washed with 1 liter of water, dried over sodium sulphate and concentrated. The oily residue was taken up in ether, whereupon crystallization occurs. 34 g (57.6% of theory) of 6-cyano-2,2-dimethyl-4-imidazol-1-yl-5-phenyl-3-hexanone were obtained as a diastereomer mixture of melting point 108° to 111° C.

Example 2

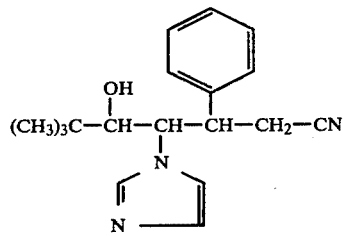

(2)

(Process variant (a); reduction step)

96.5 (0.33 mole) of 6-cyano-2,2-dimethyl-4-imidazol-1-yl-5-phenyl-3-hexanone (obtained as described in Example 1) were dissolved in 400 ml of isopropanol, and 15.12 g (0.4 mole) of sodium borohydride were added in portions at 0° to 20° C. The mixture was subsequently stirred at room temperature for 24 hours, 800 ml of 2 N hydrochloric acid were added dropwise at 0° to 10° C. and the mixture was subsequently stirred again at room temperature for 24 hours. The reaction mixture was then neutralized with 1.5 liters of saturated sodium bicarbonate solution and extracted three times with 400 ml of methylene chloride each time. The combined organic phases were washed with water, dried over sodium sulphate and concentrated. The residue was boiled up in 300 ml of diisopropyl ether, and the crystals formed on cooling were filtered off. 28.7 g (30% of theory) of 6-cyano-2,2-dimethyl-4-imidazol-1-yl-5-phenyl-3-hexanol were obtained as a diastereomer mixture of melting point 212° to 228° C.

EXAMPLE 3

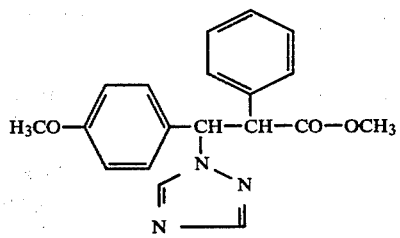

(3)

(Process variant (b))

65 g (0.24 mole) of 3-(4-methoxyphenyl)-2-phenylacrylic acid methyl ester and 67.3 g (0.98 mole) of 1,2,4-triazole were heated under reflux in the presence of 1.1 g of tribenzo-(18)-crown-6 and 8.1 g of potassium fluoride in 1 liter of acetonitrile for 240 hours. The solvent was then distilled off in vacuo, 700 ml of water were added to the residue and the mixture was extracted three times with 250 ml of methylene chloride each time. The combined organic phases were dried over sodium sulphate and concentrated. The residue was dissolved in 200 ml of acetone. 12 g of 1,5-naphthalenedisulphonic acid in 50 ml of acetone were filtered in and the precipitate formed was filtered off. This precipitate was taken up in 150 ml of saturated sodium bicarbonate solution and the mixture was extracted twice by stirring with 250 ml of methylene chloride each time. The combined organic phases were washed with 100 ml of water, dried over sodium sulphate and concentrated. The residue was recrystallized from ethyl acetate. 9.8 g of 3-(4-methoxyphenyl)-2-phenyl-3-(1,2,4-triazol-1-yl)-propionic acid methyl ester of melting point 159°–161° C. were obtained.

In the following table, compounds of the general formula

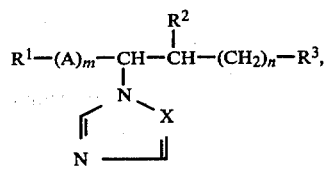

(I)

in which $R^1$, $R^2$, $R^3$, A, X, m and n have the indicated meanings, were obtained in a corresponding manner.

| Compound No. | R¹ | Aₘ | X | R² | n | R³ | Melting point (°C.) |
|---|---|---|---|---|---|---|---|
| 4 | (CH₃)₃C | CO | CH | H | 1 | CN | boiling point: 170° C./0.05 mm |
| 5 | (CH₃)₃C | CO | CH |  | 1 | —CO—OCH₃ | 118–32 |
| 6 | (CH₃)₃C | CO | CH | 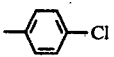 | 1 | —CO—OCH₃ | 160–66 |
| 7 | (CH₃)₃C | CO | CH |  | 1 | —CO—OC₂H₅ | 88 (decomposition) (× HCl) |
| 8 | (CH₃)₃C | CO | CH | 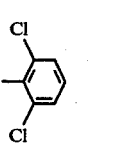 | 1 | —CO—OCH₃ | 180–202 (decomposition) (× HCl) |
| 9 | (CH₃)₃C | CO | CH | 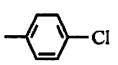 | 1 | CN | 218–43 |
| 10 | (CH₃)₃C | CO | CH | 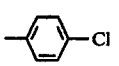 | 1 | —CO—OC₂H₅ | 57–70 (decomposition) (× HCl) |
| 11 | (CH₃)₃C | CH(OH) | CH | H | 1 | CN | 148–52 |
| 12 | (CH₃)₃C | CH(OH) | CH | 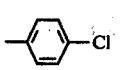 | 1 | CN | >280 (× ½ NDS) |
| 13 | (CH₃)₃C | CH(OH) | CH |  | 1 | —CO—OCH₃ | 191–98 (decomposition) |
| 14 | (CH₃)₃C | CH(OH) | CH | 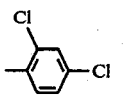 | 1 | —CO—OC₂H₅ | 130 (decomposition) (× HCl) |
| 15 | (CH₃)₃C | CH(OH) | CH | 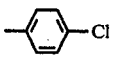 | 1 | —CO—OC₂H₅ | 270 (decomposition) |
| 16 | (CH₃)₃C | CO | N | H | 1 | CN | 62–66 |
| 17 | (CH₃)₃C | CO | N |  | 1 | CN | 120–24 |
| 18 | (CH₃)₃C | CO | N |  | 1 | —CO—OCH₃ | 93–106 |
| 19 | (CH₃)₃C | CO | N | 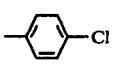 | 1 | —CO—OCH₃ | 112–114 |
| 20 | (CH₃)₃C | CO | N | 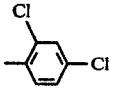 | 1 | —CO—OC₂H₅ | 128–38 |
| 21 | (CH₃)₃C | CO | N | 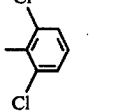 | 1 | —CO—OCH₃ | 108–32 |
| 22 | (CH₃)₃C | CO | N | 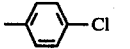 | 1 | CN | 132–52 |

-continued

| Compound No. | R¹ | $A_m$ | X | R² | n | R³ | Melting point (°C.) |
|---|---|---|---|---|---|---|---|
| 23 | (CH₃)₃C | CH(OH) | N | H | 1 | CN | 107–12 |
| 24 | (CH₃)₃C | CH(OH) | N | ⟨phenyl⟩ | 1 | CN | 123–26 |
| 25 | (CH₃)₃C | CH(OH) | N | ⟨4-Cl-phenyl⟩ | 1 | CN | 78 (decomposition) |
| 26 | (CH₃)₃C | CH(OH) | N | ⟨4-Cl-phenyl⟩ | 1 | —CO—OCH₃ | 68 (decomposition) |
| 27 | (CH₃)₃C | CH(OH) | N | ⟨phenyl⟩ | 1 | —CO—OCH₃ | 52–58 |

The fungicidal activity of compounds of the invention is illustrated by the following examples wherein the compounds according to the present invention are identified by the number (given in brackets) from the preparative examples hereinabove.

The known comparison compounds are identified as follows:

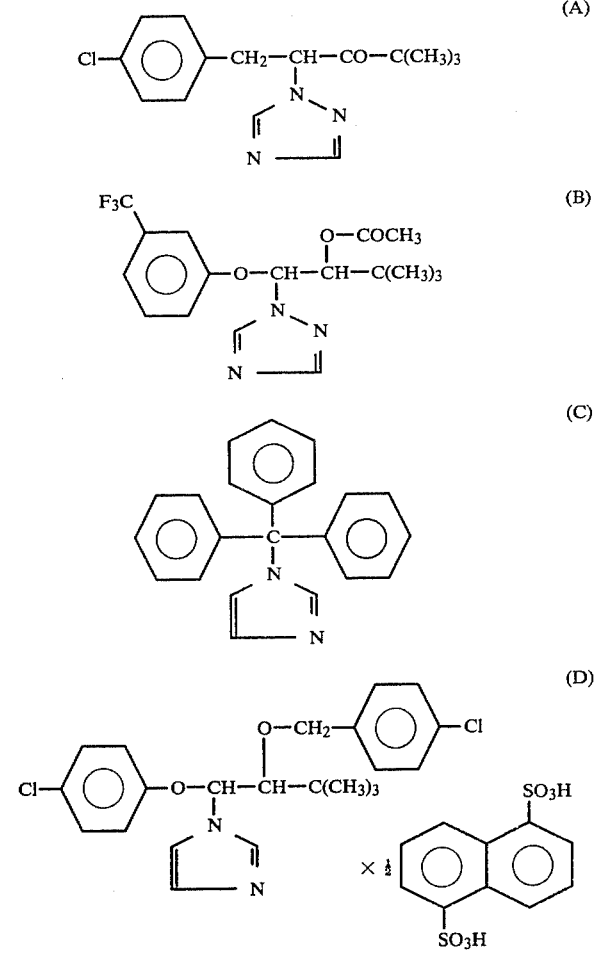

EXAMPLE 4

Podosphaera test (apple)/protective
Solvent: 4.7 parts by weight of acetone
Emulsifier: 0.3 part by weight of alkylaryl polyclycol ether
Water: 95.0 parts by weight.

The amount of active compound required for the desired concentration of the active compound in the spray liquid was mixed with the stated amount of solvent, and the concentrate was diluted with the stated amount of water which contains the stated additions.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated by dusting with conidia of the apple powdery mildew causative organism (*Podosphaera leucotricha*) and placed in a greenhouse at a temperature of 21° to 23° C. and at a relative atmospheric humidity of about 70%.

10 days after the inoculation, the infection of the seedlings was determined. The assessment data were converted to percent infection. 0% denoted no infection and 100% denoted that the plants were totally infected.

In this test, a clearly superior activity compared with the compound (A) known from the prior art was shown, for example, by the compounds (19), (20), (22) and (25).

EXAMPLE 5

Fusicladium test (apple)/protective
Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent, and the concentrate was diluted with the stated amount of water which contained the stated additions.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (*Fusicladium dendriticum*) and incubated for 18 hours in a humidity chamber at 18° to 20° C. and at a relative atmospheric humidity of 100%.

The plants then again came into a greenhouse for 14 days.

15 days after inoculation, the infection of the seedlings was determined. The assessment data were converted to percent infection. 0% denoted no infection and 100% denoted that the plants were totally infected.

In this test, a clearly superior activity compared with the compounds (A) and (C) known from the prior art was shown, for example, by the compounds (19), (4), (1), (5), (8), (9), (11) and (2).

EXAMPLE 6

Erysiphe test (Barley)/protective
Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis* f.sp. hordei.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a clearly superior activity compared with the prior art was shown, for example, by the compounds (4), (5), (6), (7), (8), (9), (12), (13), (14), (17), (18), (19), (20), (22), (23), (24) and (25).

It will be understood that the specification and examples are illustrative but not limitative of the present invention and that other embodiments within the spirit and scope of the invention will suggest themselves to those skilled in the art.

We claim:

1. An azolylalkyl derivative of the formula $$R^1-A-CH-\underset{\underset{\substack{N\\ \|\\ N}}{|}}{\overset{R^2}{CH}}-CH_2-R^3$$

in which
R$^1$ is an alkyl group with 1 to 4 carbon atoms or optionally substituted phenyl or naphthyl group,
R$^2$ is an optionally substituted phenyl or naphthyl group,
R$^3$ is a cyano group or a —CO—OR$^4$ group, and
R$^4$ is an alkyl group with 1 to 4 carbon atoms or an optionally substituted phenylalkyl or naphthylalkyl group with 1 or 2 carbon atoms in the alkyl part, the optional substituent(s) of R$^1$ and/or R$^2$ and/or R$^4$ being independently selected from halogen, alkyl with 1 to 4 carbon atoms, halogenalkyl with 1 or 2 carbon atoms and 1 to 5 identical or different halogen atoms, alkoxy and alkylthio with in each case 1 or 2 carbon atoms, and phenyl,
A is a keto group or a CH(OH) group, and
X is a nitrogen atom or the CH group, or a physiologically acceptable addition product thereof with an acid or a metal salt.

2. A fungicidal composition comprising a fungicidally effective amount of a compound or addition product according to claim 1 in admixture with a diluent.

3. A method of combating fungi comprising applying to the fungi, or to a habitat thereof, a fungicidally effective amount of a compound or addition product according to claim 1.

4. An azolylalkyl derivative of the formula $$R^1-A-CH-\underset{\underset{\substack{N\\ \|\\ N}}{|}}{\overset{R^2}{CH}}-CH_2-R^3$$

in which
R$^1$ is an alkyl group with 1 to 4 carbon atoms,
R$^2$ is a hydrogen atom, an alkyl group with 1 to 4 carbon atoms or an optionally substituted phenyl or naphthyl group,
R$^3$ is a cyano group or a —CO—OR$^4$ group, and
R$^4$ is an alkyl group with 1 to 4 carbon atoms or an optionally substituted phenylalkyl or naphthylalkyl group with 1 or 2 carbon atoms in the alkyl part, the optional substituent(s) of R$^2$ and/or R$^4$ being independently selected from halogen, alkyl with 1 to 4 carbon atoms, halogenoalkyl with 1 or 2 carbon atoms and 1 to 5 identical or different halogen atoms, alkoxy and alkylthio with in each case 1 or 2 carbon atoms, and phenyl,
A is a keto group or a CH(OH) group, and
X is a nitrogen atom or the CH group, or a physiologically acceptable addition product thereof with an acid or a metal salt.

5. A compound or addition product according to claim 4, in which
A is CH(OH).

6. A compound according to claim 4, in which R$^1$ is a tert.-butyl or isopropyl group; R$^2$ is a hydrogen atom, methyl, ethyl, n-propyl or isopropyl group, or a phenyl group which is optionally substituted by fluorine, chlorine, methyl, ethyl, isopropyl, methoxy or phenyl; R$^3$ is a cyano group or a —CO—OR$^4$ group; R$^4$ is a methyl, ethyl or propyl group, or a benzyl group which is optionally substituted by fluorine, chlorine or methyl, or an addition product with a physiologically acceptable acid selected from the group consisting of a hydrogen halide acid, phosphoric acid, nitric acid, sulphuric acid, a monofunctional or bifunctional carboxylic or hydroxycarboxylic acid or a sulphonic acid, or with a metal salt in which the metal is copper, zinc, manganese, magnesium, tin, iron or nickel and the anion is derived from hydrochloric, hydrobromic, phosphoric, nitric or sulphuric acid.

7. A compound according to claim 4, wherein such compound is 4-(1,2,4-triazol-1-yl)-6,6-dimethyl-3-(p-chloro-phenyl)-5-keto-heptanoic acid methyl ester of the formula

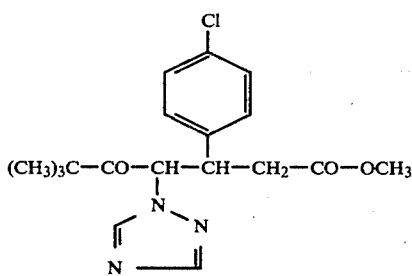

or a physiologically acceptable addition product thereof with an acid or a metal salt.

8. A compound according to claim 4, wherein such compound is 4-(1,2,4-triazol-1-yl)-6,6-dimethyl-3-(2,4-dichlorophenyl)-5-keto-heptanoic acid ethyl ester of the formula

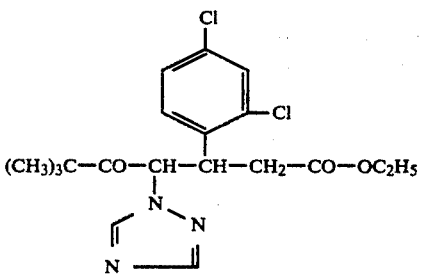

or a physiologically acceptable addition product thereof with an acid or a metal salt.

9. A compound according to claim 4, wherein such compound is 6-Cyano-2,2-dimethyl-5-(4-chlorophenyl)-4-(1,2,4-triazol-1-yl)-3-hexanone of the formula

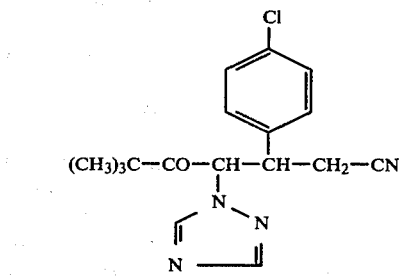

or a physiologically acceptable addition product thereof with an acid or a metal salt.

10. A fungicidal composition comprising a fungicidally effective amount of a compound or addition product according to claim 4 in admixture with a diluent.

11. A method of combating fungi comprising applying to the fungi, or to a habitat thereof, a fungicidally effective amount of a compound or addition product according to claim 4.

12. The method according to claim 11, wherein such compound is
4-(1,2,4-triazol-1-yl)-6,6-dimethyl-3-(p-chlorophenyl)-5-keto-heptanoic acid methyl ester,
4-(1,2,4-triazol-1-yl)-6,6-dimethyl-3-(2,4-dichlorophenyl)-5-keto-heptanoic acid ethyl ester or
6-Cyano-2,2-dimethyl-5-(4-chlorophenyl)-4-(1,2,4-triazol-1-yl)-3-hexanone or a physiologically acceptable addition product thereof with an acid or a metal salt.

13. 3-(4-Methoxyphenyl)-2-phenyl-3-(1,2,4-triazol-1-yl)propionic acid methyl ester of the formula

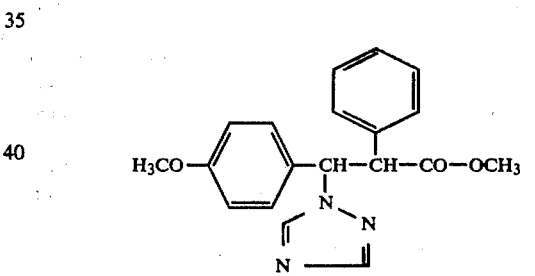

or a physiologically acceptable addition product thereof with an acid or a metal salt.

14. A fungicidal composition comprising a fungicidally effective amount of a compound or addition product according to claim 13 in admixture with a diluent.

15. A method of combating fungi comprising applying to the fungi, or to a habitat thereof, a fungicidally effective amount of a compound or addition product according to claim 13.

* * * * *